(12) United States Patent
Nakatani et al.

(10) Patent No.: US 7,641,384 B2
(45) Date of Patent: Jan. 5, 2010

(54) THERMAL ANALYSIS SYSTEM AND METHOD OF DRYING THE SAME

(75) Inventors: Rintaro Nakatani, Chiba (JP); Ryoichi Kinoshita, Chiba (JP); Shinya Nishimura, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 190 days.

(21) Appl. No.: 11/879,554

(22) Filed: Jul. 18, 2007

(65) Prior Publication Data

US 2008/0025364 A1 Jan. 31, 2008

(30) Foreign Application Priority Data

Jul. 26, 2006 (JP) .............................. 2006-203849

(51) Int. Cl.
*G01K 17/02* (2006.01)
(52) U.S. Cl. .......................................... 374/31; 374/33
(58) Field of Classification Search .................. 374/31, 374/33
See application file for complete search history.

(56) References Cited

U.S. PATENT DOCUMENTS

2008/0080591 A1* 4/2008 Tanaka et al. ................ 374/179

2008/0279249 A1* 11/2008 Nagasawa et al. ............. 374/11

FOREIGN PATENT DOCUMENTS

JP H10-104182 4/1998

* cited by examiner

*Primary Examiner*—Andre J Allen
(74) *Attorney, Agent, or Firm*—Brinks Hofer Gilson & Lione

(57) ABSTRACT

To enable the reduction in working efforts by hand by performing control a drying operation by appropriately selecting dry conditions depending on the connection mode of the cooling device, and removal of moisture and the like without fail. The thermal analysis system uses a heater and a cooling device to raise and decrease the temperature inside the purge box. In the drying method for the thermal analysis system, the drying operation is performed by: previously setting dry conditions depending on the connection mode of the cooling device; starting control of an opening time dry process upon activation of the thermal analysis system; supplying a predetermined amount of dry gas into the purge box in accordance with the dry conditions corresponding to the selected connection mode of the cooling device with the cooling device kept off; and making the temperature control module control the temperature of the dry gas.

8 Claims, 8 Drawing Sheets

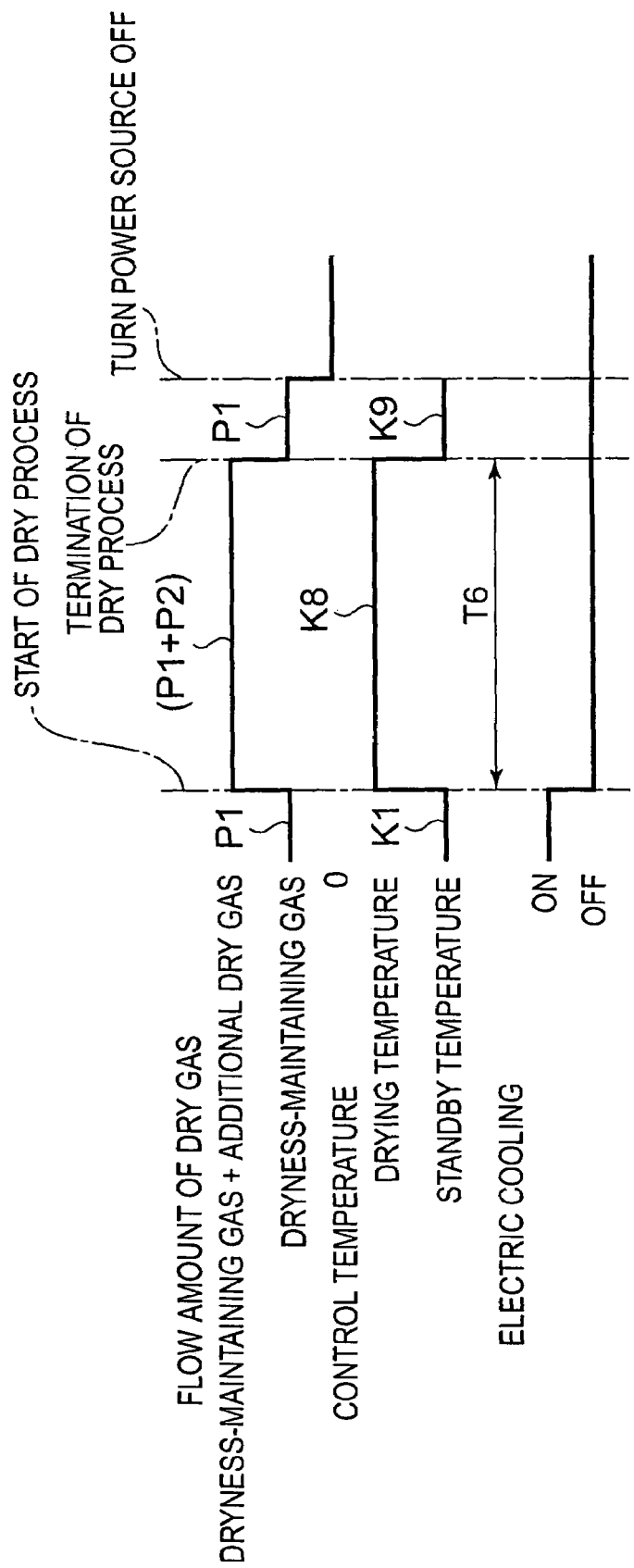

THERMAL ANALYSIS SYSTEM AND METHOD OF DRYING THE SAME

This application claims priority under 35 U.S.C. §119 to Japanese Patent Application No. JP2006-203849 filed Jul. 26, 2006, the entire content of which is hereby incorporated by reference.

BACKGROUND OF THE INVENTION

The present invention relates to a thermal analysis system such as a differential scanning calorimeter and a method of drying the same.

Conventionally, with a thermal analysis system, such as a differential scanning calorimeter, having a furnace body therein, an analysis has been performed by: loading a sample (a specimen) in the furnace body; using a heating device and a cooling device to raise and decrease the temperature of the sample to change the sample in temperature; and measuring absorption and radiation of heat by the sample in the form of an amount of heat. During such measurements, the temperature of the furnace body is lowered to e.g. a temperature of −70 to −150° C. constantly or temporarily. That is to say, the furnace body portion and its surroundings and the like remain cooled successively, and stay in the situations easy to cause condensation. Particularly when a sample is loaded into and unloaded from the thermal analysis system, opening an opening-and-closing cover of the thermal analysis system causes the outside air to flow into the furnace body and the inside of the case, which can cause condensation on the furnace body portion and its surroundings, and further on a temperature sensor such as a thermocouple and others, leading to adhesion of water droplets and frost thereon. When measurements are performed under the situation where the frost is thus formed, fluctuations arise in the measured temperatures to generate noises in data to be measured. This has been a cause of the impossibility of acquisition of exact measurement values. Hence, a method including uninterruptedly supplying a predetermined amount of dry gas to the thermal analysis system thereby to keep the inside of the analysis system in a dried state, and manually supplying a large amount of additional dry gas on an as-needed basis has been practiced.

Further, a method of performing automatic supply of dry gas instead of manual supply like this thereby to suppress the occurrence of condensation has been disclosed in e.g. JP-A-10-104182.

In Patent Document 1, an open-and-close sensing switch for sensing open and close states of an opening-and-closing cover provided on an outer case making an outside housing of the thermal analysis system is provided, and the supply of dry gas is controlled by ON/OFF signals from the open-and-close sensing switch. In other words, as a large amount of dry gas is supplied to the surroundings of the furnace body inside the thermal analysis system when the opening-and-closing cover is opened for loading and unloading a sample, intrusion of the outside air through the opening-and-closing cover can be cut thereby to prevent condensation and frost from forming around the furnace body.

However, as for the thermal analysis system used in JP-A-10-104182, it is expected that the humidity inside the thermal analysis system is equivalent to that of the outside air at the time when the power source is activated, i.e. before the cooling device is actuated. In that situation, actuating the cooling device will cause generation of condensation and frost and the like in the thermal analysis system owing to the moisture remaining in the analysis system. The thermal analysis system has the disadvantage that the moisture, particularly the moisture adhering to a cooling module and the like cannot be removed easily even by supplying dry gas or heating surroundings of a specimen thereafter. Therefore, the moisture which has adhered to the inside of the analysis system at the time of measurement cannot be removed sufficiently only by automatically supplying an additional dry gas at the time of opening and closing the opening-and-closing cover as described in JP-A-10-104182. This moisture causes the temperature to fluctuate and generates noises in measurement data.

In addition, a measure including manually supplying an additional dry gas thereby to dry the inside of the analysis system, and heating a heater block around a specimen thereby to accelerate the drying before the cooling device is actuated is taken separately. However, there is the problem that in the case where the drying is performed through both drying by gas and heating of the heater block before actuation of the cooling device, excessively raising the drying temperature damages the cooling module (especially, a leading end of the cooling rod) inserted in and connected with the thermal analysis system when the cooling device is e.g. an electric cooling device. Since the preferable drying time and the drying temperature vary depending on a cooling method including the type of a cooling device and its connection mode as stated above, their management has been a difficult and troublesome work.

The invention was made in consideration of the foregoing problems. Therefore, it is an object of the invention to provide a thermal analysis system and its drying method, by which working efforts by hand can be reduced by adequately selecting a dry condition in accordance with the connection mode of the cooling device and controlling a drying operation and moreover the moisture and the like can be removed without fail.

SUMMARY OF THE INVENTION

To achieve the above-described object, a thermal analysis system in association with the invention is a thermal analysis system having a furnace body portion including a heater block into which a specimen is loaded, a cooling block connected with the heater block, and a purge box making an outside housing of the heater block and cooling block, which is characterized by having a furnace body portion-drying means for drying the furnace body portion for a predetermined time in response to activation of the thermal analysis system.

In addition, a method of drying a thermal analysis system in association with the invention is a method of drying a thermal analysis system having a heater block for heating a specimen, a cooling block connected with the heater block, and a purge box making an outside housing of the heater block and cooling block, which is characterized by having a step of drying the furnace body portion before thermal analysis measurement of the specimen upon activation of the thermal analysis system.

In the invention, the inside of the purge box begins to be dried upon the activation of the thermal analysis system, and therefore the moisture including condensation and frost, which has adhered to the inside of the system before actuation of the cooling device, can be removed at the time before measurement without fail. That is, as the box inside is brought to a dried state before thermal analysis measurement of a specimen, the noise generation in the data in measurement owing to moisture is avoided, and thus a precise measurement can be performed.

Also, it is preferable that in the thermal analysis system in association with the invention, the furnace body portion-drying means include: a gas-inflow means for letting a drying gas flow into the furnace body portion; and a heater block temperature-controlling means for controlling a temperature of the heater block.

In the invention, the gas-inflow means supplies the dry gas into the purge box, and the heater block temperature-controlling means conducts temperature control of the temperature of the heater box, whereby the drying operation can be performed.

In addition, it is preferable that in the thermal analysis system according to the invention, the furnace body portion-drying means change a gas-inflow condition, and a control temperature condition depending on a type of a cooling device connected with the cooling block.

In the invention, drying can be performed in accordance with dry conditions, i.e. an amount of dry gas supply, and a drying temperature, suitable for the type of the cooling device connected with the cooling block.

It is preferable that in the thermal analysis system according to the invention, when the cooling device be an electric cooling device, the heater block temperature-controlling means make the temperature of the heater block a first temperature with the cooling device kept off, and make the temperature a second temperature higher than the first temperature after confirmation of activation of the electric cooling device.

The invention enables: drying the furnace body portion at the first temperature so high as not to damage the cooling module of the electric cooling device; thereafter actuating the electric cooling device thereby to cool a surrounding portion of the cooling module (cooling rod); and then raising the control temperature to a higher second temperature to dry the furnace body portion. Therefore, two stages of drying can be performed elaborately.

A thermal analysis system according to the invention is a thermal analysis system having a furnace body portion including a heater block into which a specimen is loaded, a cooling block connected with the heater block, and a purge box making an outside housing of the heater block and cooling block, which is characterized by having a furnace body portion-drying means for drying the furnace body portion for a predetermined time before a power source is shut off in response to a manipulation for ordering end-of-work of the thermal analysis system.

In the invention, drying of the inside of the purge box is carried out by performing a manipulation for ordering the end-of-work at the closing time, whereby condensation can be prevented from occurring inside the purge box when the thermal analysis system is used the next time. Particularly, in the case of using the electric cooling device, the cooling block remains cooled for a while even after the power source of the thermal analysis system has been cut, and condensation sometimes occurs around the cooling block. However, such cooled state in the purge box can be prevented by performing the drying before the power source is cut, whereby the occurrence of condensation like this can be suppressed.

It is preferable that in the method of drying a thermal analysis system according to the invention, the drying step be a step including supplying a dry gas into the purge box, and managing a temperature of the heater block with a temperature control module thereby to control a drying operation.

In the invention, drying control, for example depending on the connection mode of the cooling device can be performed by controlling the amount of gas flow of the dry gas supplied into the purge box and the temperature of the heater block.

It is preferable that the method of drying a thermal analysis system according to the invention have: a step of previously setting a dry condition depending on a connection mode of the cooling device; a step of starting control of an opening time dry process simultaneously with activation of the thermal analysis system; a step of selecting the connection mode of the cooling device; and a drying step of drying the furnace body portion before thermal analysis measurement of the specimen in accordance with the dry condition corresponding to the selected cooling device connection mode.

In the invention, at the time when the power source of the thermal analysis system is turned on, the control of the opening time dry process is started. Further, by performing a manipulation for selecting the connection mode of the cooling device for cooling the thermal analysis system, the drying operation can be controlled automatically in accordance with dry conditions set depending on the connection mode of the cooling device, i.e. amount of dry gas supply, a time for the supply, a drying temperature and others. Hence, it becomes possible to eliminate the labor as in a conventional case, such as performing a manual manipulation and management based on the dry conditions.

It is preferable that in the method of drying a thermal analysis system according to the invention, when the cooling device be an electric cooling device, the temperature of the heater block be controlled to primarily dry the system at a first temperature with the electric cooling device kept off, and then the cooling device be actuated to secondarily dry the system at a second temperature higher than the first temperature.

The invention enables, for example in the case of electric cooling, controlling the temperature of the heater block, primarily drying the furnace body portion at the first temperature so high as not to damage the cooling module of the electric cooling device, thereafter actuating the electric cooling device thereby to cool a surrounding portion of the cooling module (cooling rod), then raising the temperature to the higher second temperature thereby to secondarily dry the furnace body portion. Therefore, two stages of drying can be performed elaborately. Thus, part of the moisture which cannot be removed through the primary drying perfectly can be removed through the secondary drying at the second temperature without fail hereby to finish the drying.

In addition, it is preferable that in the method of drying a thermal analysis system according to the invention, when the cooling device is an electric cooling device, a connection mode of the thermal analysis system and the electric cooling device is confirmed before the secondary drying is performed.

In the invention, the connection mode of the electric cooling device selected at the time of starting the control of the opening time dry process can be reconfirmed before the secondary dry process. In other words, the working stage of the electric cooling device can be confirmed before the furnace body portion is dried at a high temperature in secondary drying to prevent the electric cooling device from being damaged. In addition, it is also possible to check whether or not there is a mistake in selecting the cooling method. A method for such confirmation includes: for example setting the control temperature so that the temperature of the heater block is made a temperature lower than the first temperature and equal to a room temperature or lower; making judgment that the electric cooling device is working normally in the case where the heater block temperature lowers to the control temperature; and continuously performing secondary drying at a high temperature (second temperature). In contrast, in the case where the heater block temperature does not lower to the control temperature, it is judged that the electric cooling device is not working normally. Then, an error notice is presented for example, and the connection mode of the electric cooling device can be reconfirmed.

Further, it is preferable that in the method of drying a thermal analysis system according to the invention, when a manipulation for ordering end-of-work of the measurement is performed, control of a closing time dry process is started, and a drying operation is performed by supplying a predetermined amount of the dry gas into the purge box.

In the invention, the control of drying is executed by performing a manipulation for ordering the end-of-work at the closing time, whereby condensation can be prevented from occurring inside the purge box when the thermal analysis system is used the next time. Particularly in the case of using the electric cooling device, the cooling block remains cooled for a while even after the power source of the thermal analysis system has been cut, and condensation sometimes occurs around the cooling block. However, such cooled state in the purge box can be prevented by performing the closing time dry process, whereby the occurrence of condensation like this can be suppressed.

Still further, it is preferable that in the method of drying a thermal analysis system in association with the invention, after the drying operation in the closing time dry process has been terminated, control is performed so that the power source of the thermal analysis system is cut off automatically.

In the invention, the thermal analysis system may include a main power cutoff device, for example, in which the thermal analysis system can be cut off at the time of termination of drying automatically by making control so that the main power cutoff device is actuated after a predetermined time has elapsed.

Furthermore, it is preferable that in the method of drying a thermal analysis system according to the invention, the drying is performed at a temperature the same as that of a surrounding portion of the thermal analysis system in the closing time dry process.

With the invention, even when a specimen is left loaded in the thermal analysis system after measurement, the trouble that the specimen melts can be avoided because the drying temperature is not so high but the same as that of a surrounding portion of the thermal analysis system.

In accordance with a thermal analysis system of the invention and its drying method, when the thermal analysis system is activated, drying of the inside of the purge box can be started, whereby moisture such as condensation and frost, which has adhered to the inside before actuation of the cooling device, can be removed at the time before measurement without fail. Hence, the noise generation in the data in measurement owing to such moisture is avoided, and thus a precise measurement can be performed. In addition, the furnace body portion-drying means which performs dry control of the dry conditions depending on the connection mode of the cooling device, i.e. an amount of supply of the dry gas, a time for the supply, a drying temperature, and others, can eliminate the labor to manage the dry conditions through a manual manipulation as in a conventional case, and thus the inside of the system can be dried efficiently and without fail. Further, in the case where the system is not used for a long time, the system can be dried appropriately in using the system even if the dry gas is not kept flowing. Therefore, the thermal analysis system and its drying method are effective in preventing the waste of dry gas kept flowing for a long time.

The thermal analysis system of the invention can be made to control an operation of drying the inside of the purge box by performing a manipulation for ordering the end-of-work at the closing time. Therefore, it is possible to avoid the occurrence of condensation inside the purge box when the thermal analysis system is used next time.

BRIEF DESCRIPTION OF THE DRAWINGS

FIG. 8 is a sequence diagram of the finishing time dry process.

DETAILED DESCRIPTION OF PREFERRED EMBODIMENTS

A thermal analysis system in accordance with an embodiment of the invention and its drying method will be described below with reference to FIGS. 1 to 8.

Figure 1:
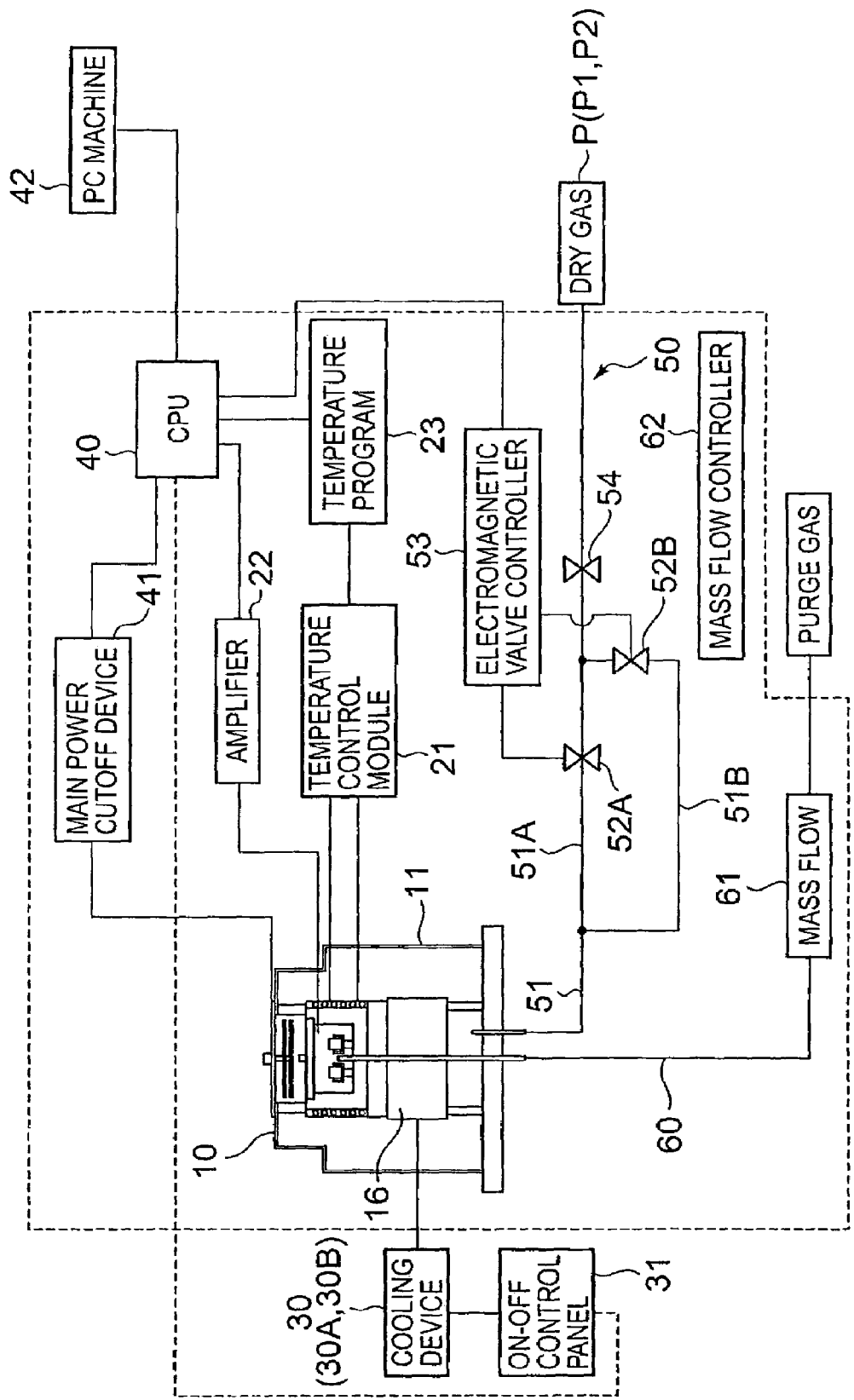
FIG. 1 is a block diagram for showing a general outline of a drying method of a thermal analysis system in accordance with an embodiment of the invention.
Figure 2:
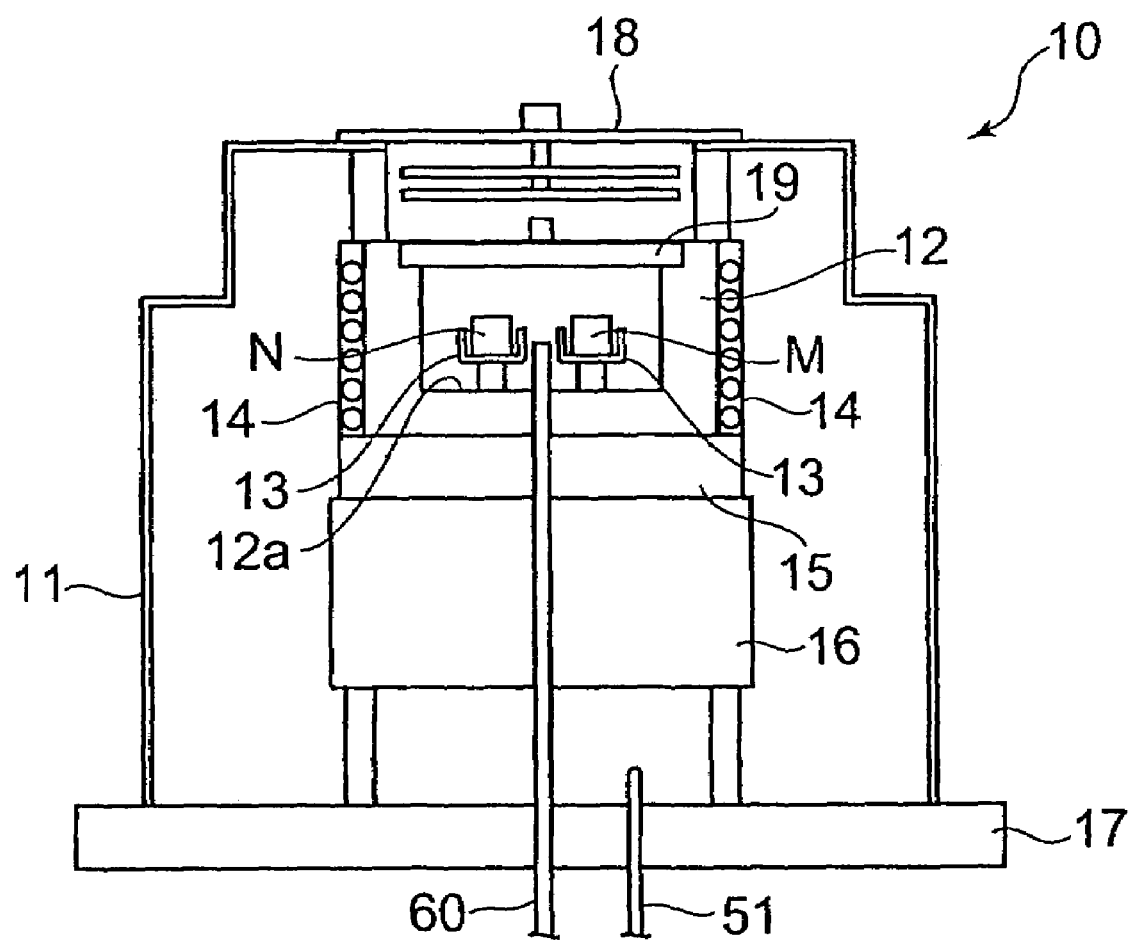
FIG. 2 is a view showing a thermal analysis system.
Figure 3:
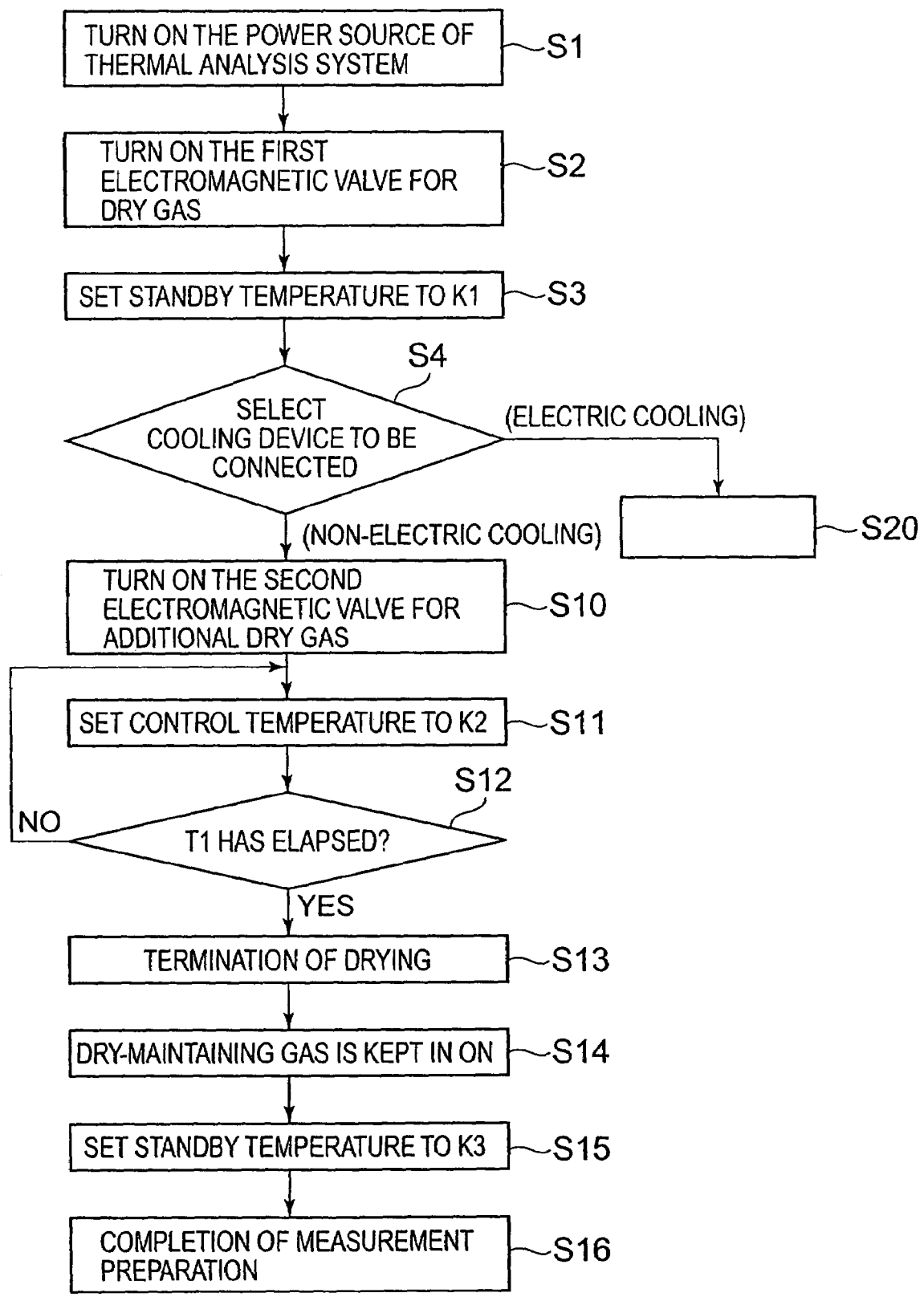
FIG. 3 is a flow chart of an opening time dry process when non-electric cooling is selected.
Figure 4:
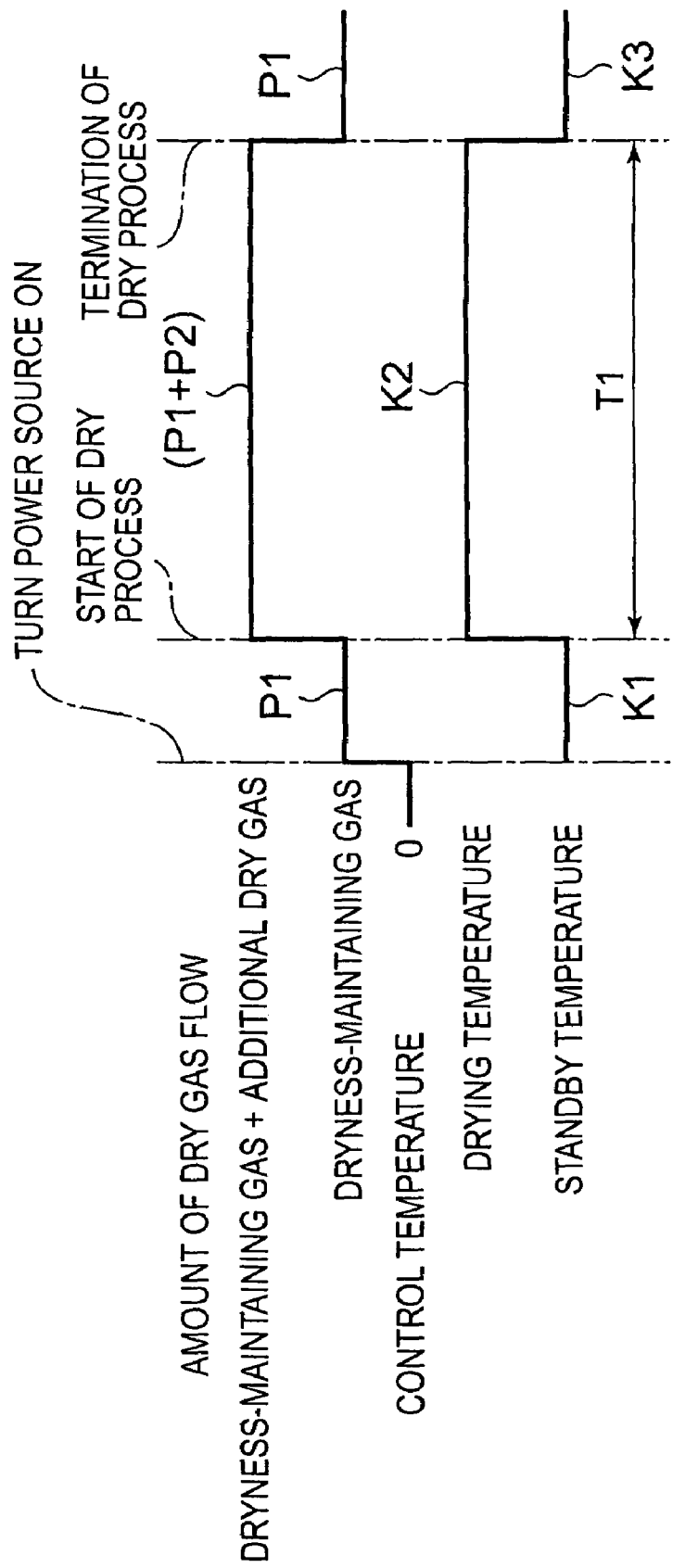
FIG. 4 is a sequence diagram of the opening time dry process when non-electric cooling is selected.
Figure 5:
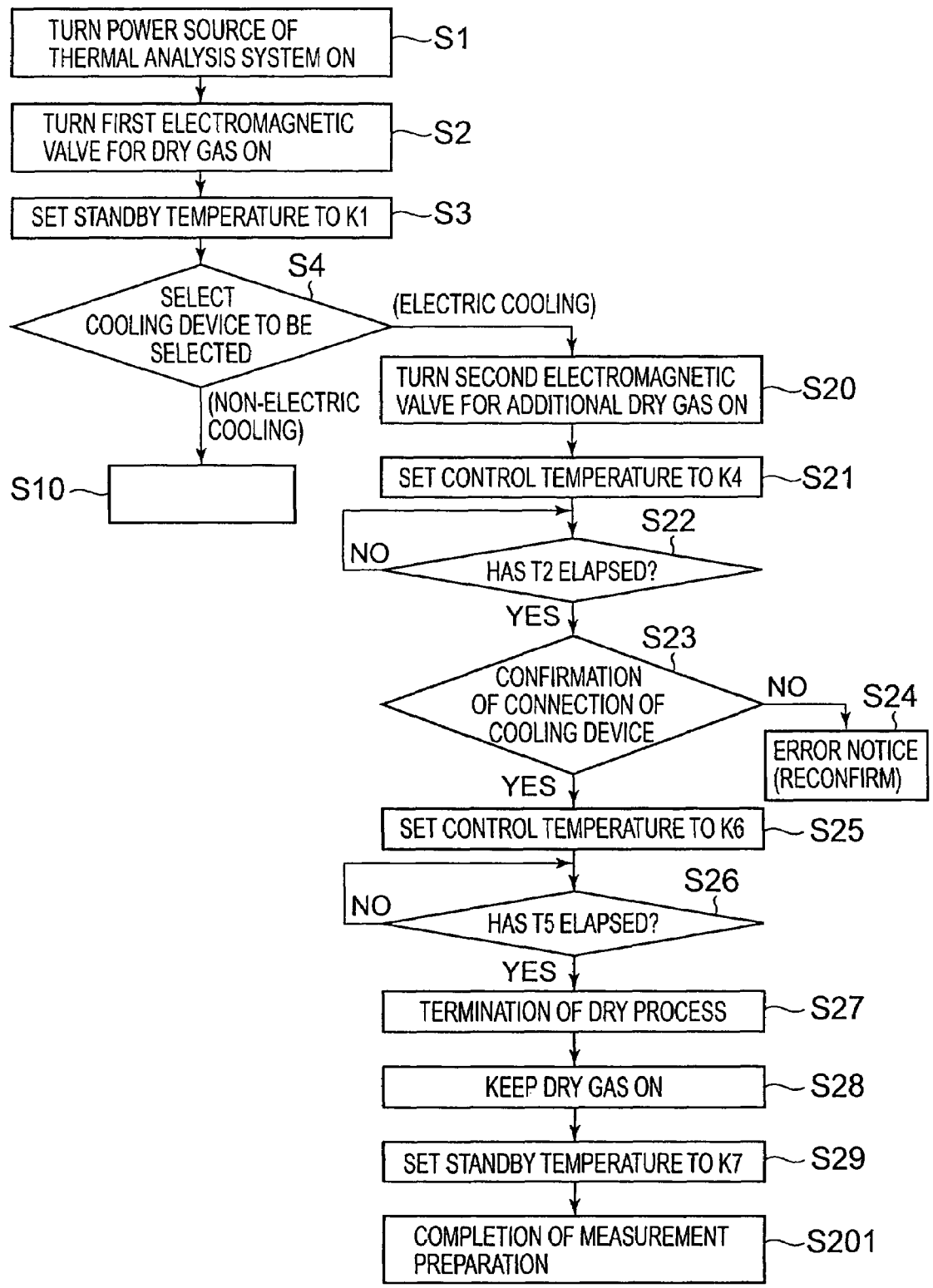
FIG. 5 is a flow chart of an opening time dry process when electric cooling is selected.
Figure 6:
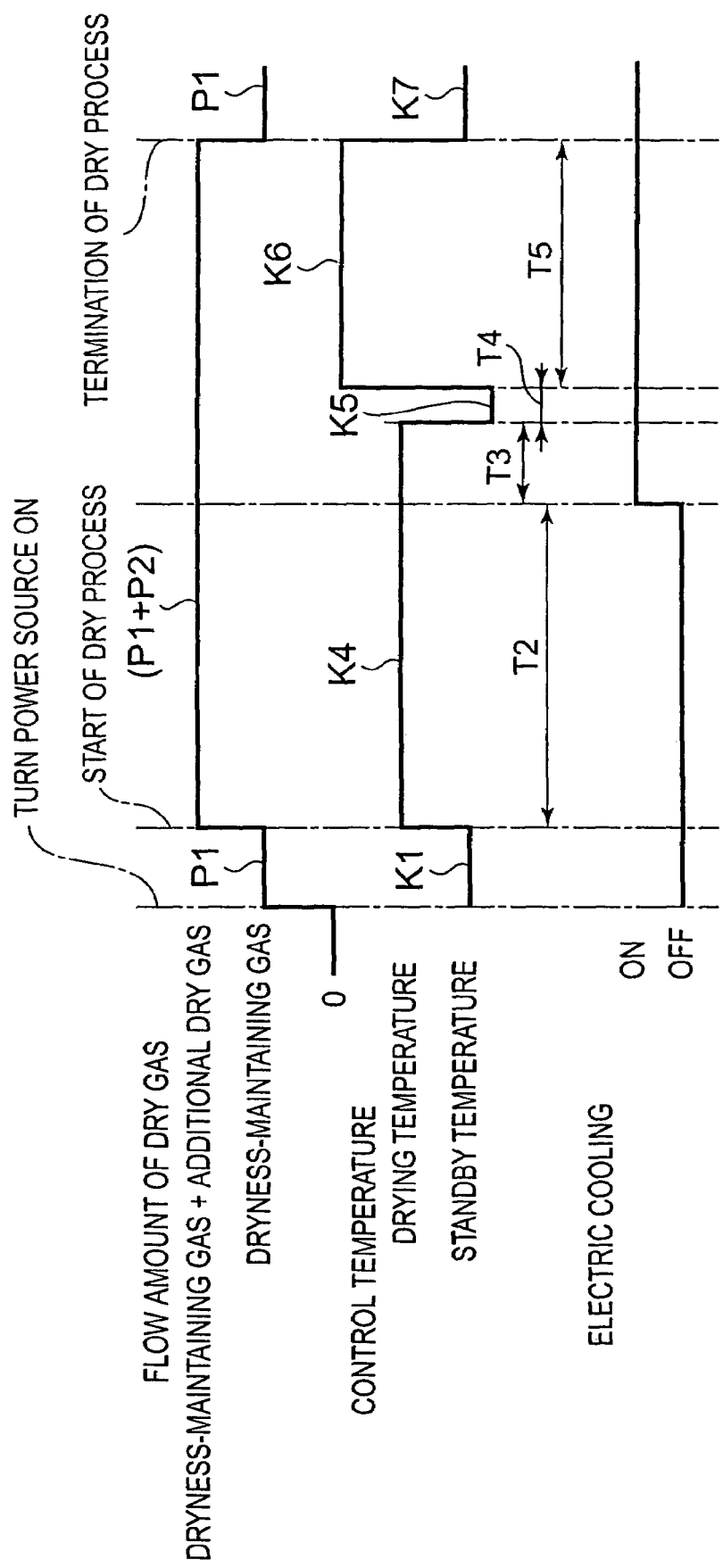
FIG. 6 is a sequence diagram of the opening time dry process when electric cooling is selected.
Figure 7:
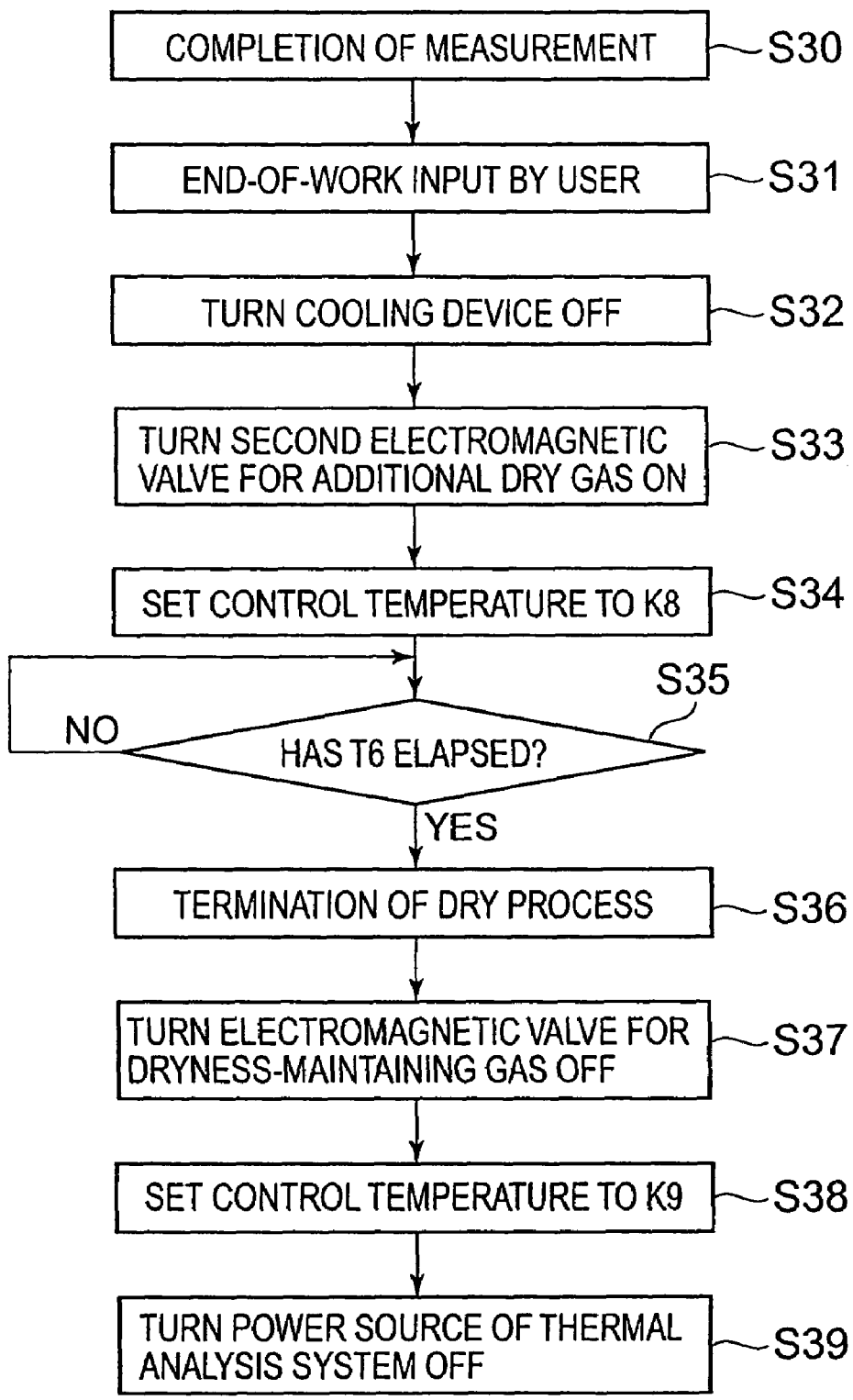
FIG. 7 is a flow chart of a finishing time dry process.

FIG. 1 is a block diagram for showing a general outline of a drying method of a thermal analysis system in accordance with an embodiment of the invention. FIG. 2 is the view showing a thermal analysis system. FIG. 3 is a flow chart of an opening time dry process when non-electric cooling is selected. FIG. 4 is a sequence diagram of the opening time dry process when non-electric cooling is selected. FIG. 5 is a flow chart of an opening time dry process when electric cooling is selected. FIG. 6 is a sequence diagram of the opening time dry process when electric cooling is selected. FIG. 7 is a flow chart of a finishing time dry process. FIG. 8 is a sequence diagram of the finishing time dry process.

As shown in FIG. 1, the method of drying a thermal analysis system in accordance with the embodiment is adopted for a thermal analysis system 10 such as a differential scanning calorimeter capable of measuring amounts of absorption and radiation of heat by performing thermal analysis for the purpose of detecting physical properties' changes (structural phase transition, thermal variance, melting, crystallization, etc.) caused in a substance.

A structure of the thermal analysis system 10 will be described with reference to the drawings, first. As shown in FIG. 2, the thermal analysis system 10 in accordance with this embodiment has a heat sink 12 (heater block) provided in a purge box 11 forming an outside housing, in which the heat sink 12 therein accepts a sample (specimen) M targeted for measurement and a standard sample N making a thermally inactive reference substance. In addition, the thermal analysis system uses a temperature sensor (not shown) such as a thermocouple to detect the difference in temperature between the sample M and the standard sample N while raising and decreasing the temperature of the heat sink 12, thereby to measure a flow rate of heat absorbed and radiated by the sample M per unit time. The sample M and the standard sample N are put in sample holders 13, 13 individually attached on a bottom plate 12a of the heat sink 12, which are positioned in substantially central portions of the inside of the heat sink 12. Herein, the sample M is a substance targeted for measurement, and the standard sample N is a thermally inactive substance and put in the sample holder 13 identical in characteristics to that for the sample M.

In addition, the thermal analysis system 10 is provided with a heater 14 (heating device) for heating the heat sink 12. By heating of the heat sink 12 by the heater 14, the temperature of the sample M can be raised to e.g. about 500° C. to perform a measurement. Also, the thermal analysis system 10 is provided with a cooling block 16 for cooling the heat sink 12 from below through a thermal conductor 15 for the purpose of decreasing the temperature of the sample M to e.g. not more than about −150° C. below a room temperature and performing a measurement.

As shown in FIG. 2, the thermal analysis system is fitted with the heat sink 12, heater 14, thermal conductor 15 and cooling block 16 placed on the pedestal 17 in the purge box 11. In a top portion of the purge box 11 is formed an opening. An outer lid 18 which can be closed and opened by hand or electricity is provided for the opening. At the time of closing the outer lid 18, the inside of the purge box 11 can be sealed. Here, a furnace body portion of the invention corresponds to a combination of the purge box 11 and a space in the purge box 11 where the heat sink 12 and cooling block 16 are positioned.

To uniformize the distribution of temperature in the heat sink 12, the heat sink 12 has the form of a thick receptacle produced with a metal having a good thermal conductivity such as silver or copper, and an inner lid 19 made of the same metal provided in its an upper end opening portion.

The heater 14 shown in FIG. 2 is a heating means for heating the heat sink 12 as described above. As the heater is adopted an electric heater arranged in the form of a coil so that it surrounds the side face of the heat sink 12. Incidentally, it is possible to use a heater other than an electric heater like this, as a matter of course.

As shown in FIG. 1, the heater 14 is controlled by a temperature control module 21 (to be described later). Also, in the heat sink 12, a temperature sensor (not shown) such as a thermocouple for detecting the temperature of the heat sink 12 is provided.

As shown in FIG. 1, the temperatures of the sample M and standard sample N detected by the temperature sensor are individually sent to an amplifier 22 and sent as a differential scanning calorimetric signal (hereinafter referred to as DSC signal) to a CPU 40. Then, while making the temperature control module 21 control the temperature of the heat sink 12 following a predetermined temperature program 23, the thermal analysis system 10 measures DSC signals from the differences in temperature between the sample M and the standard sample N at this time and makes a data processing unit (CPU 40) perform a thermal analysis.

Herein, the CPU 40 has a storing module. The CPU is connected to a personal computer (hereinafter referred to as "PC machine 42" for short), and connected with an amplifier 22, a temperature program 23, an electromagnetic valve controller 53 of a dry gas supplying means 50, which is to be described later, and a main power cutoff device 41.

In addition, while the detail is to be described later, the storing module of the CPU 40 holds dry conditions (e.g. an amount of dry gas supply, a drying time, a drying temperature, and ON/OFF of the cooling device) set previously, and the dry conditions vary depending on the connection mode of the cooling device (which has two kinds of such mode, i.e. an electrically cooling mode and a mode other than the electrically cooling mode in this embodiment). Further, the CPU 40 is arranged so that during execution of dry control, it controls the constituents based on the dry conditions, and dries the inside of the thermal analysis system 10 (purge box 11) in accordance with a suitable dry condition.

Meanwhile, when the control of the closing time dry process to be described later is exercised, the main power cutoff device 41 turns OFF the power source of the thermal analysis system 10 after termination of the drying. The details of the main power cutoff device 41 will be described in the description on the drying method to be presented later.

Also, as a purge gas is kept flowing into the heat sink 12 at an amount of flow of e.g. about 50 mL/min during the time of a measurement usually, a purge gas duct 60 (the detail of which will be described later) for supplying a purge gas into the heat sink 12 from the outside is disposed in the thermal analysis system 10.

The cooling block 16 shown in FIG. 2 is a cooling means for cooling the heat sink 12. As shown in FIG. 1, the cooling block 16 is connected with a selected cooling device 30 such as a liquid nitrogen type cooling device (marked with 30A) or an electric cooling device (marked with 30B) provided outside the purge box 11 so that the cooling device can be removed (replaced).

The liquid nitrogen type cooling device 30A can force a coolant such as nitrogen gas to circulate through the inside of the cooling block 16 while adjusting the amount of gas flow thereby to change the temperature of the cooling block 16. The electric cooling device 30B cools the cooling block 16 at a substantially constant temperature rate in the state where the leading end of the cooling rod (not shown) is inserted in the cooling block 16 so that the leading end reaches the center of the cooling block substantially.

Also, the cooling device 30 is connected with the CPU 40 through an ON/OFF control panel 31. Therefore, the CPU 40 controls ON/OFF of the cooling device 30, and manages the operations for activation and deactivation of the cooling device as required.

As shown in FIG. 1, the temperature control module 21 is connected to the CPU 40 through the temperature program 23. The temperature control module is a device which controls an amount of heating by the heater 14 and an amount of heat absorption by the cooling block 16 so that the temperature of the heat sink 12 follows the predetermined temperature program 23.

Specifically, the temperature control module 21 makes the heater 14 increase the amount of heating when the heat sink 12 reaches a temperature lower than a temperature set by the temperature program 23, and forces the heater 14 reduce the amount of heating or stop heating when the temperature of the heat sink 12 is excessively high. In the cases of lowering the temperature of the heat sink 12 to a temperature lower than a room temperature and dropping the temperature sharply, the temperature control module 21 adjusts the amount of heat absorption with the cooling device 30. However, since the amount of heat absorption by the cooling block 16 cannot be adjusted in the case where the cooling block is cooled at a substantially constant temperature rate at all times as the electric cooling device 30B does, the temperature control module 21 controls only the heater 14 thereby to control the temperature.

Herein, a combination of the temperature sensor, the temperature control module 21, the amplifier 22, the temperature program 23 and the CPU 40, which have been described above in this embodiment, corresponds to a heater block temperature-controlling means of the invention.

Now, the thermal analysis system 10 is provided with the dry gas supplying means 50 (which corresponds to a gas-inflow means of the invention), as shown in FIG. 1. In the dry gas supplying means 50, a dry gas duct 51 for supplying a dry gas P into the purge box 11 from the outside of the thermal analysis system 10 through an electromagnetic valve 52 is disposed. Further, the dry gas supplying means includes an electromagnetic valve controller 53 for controlling the opening and closing of the electromagnetic valve 52. The dry gas duct 51 is arranged so as to supply the dry gas P from a bottom portion inside the purge box 11. The dry gas P is a gas which contains very little moisture to prevent condensation and deposition of frost. The dry gas may be the same inert gas as the purge gas; otherwise e.g. an air with the dampness removed may be used as the dry gas.

The dry gas duct 51 has a branch-confluent portion in a middle portion thereof, one branch beyond the point is made a first branch duct 51 A forming a flow path of a dryness-maintaining gas P1 to be described later, and the other branch is made a second branch duct 51B forming a flow path of an additional dry gas P2 to be described later. Moreover, the first branch duct 51A is provided with a first electromagnetic valve 52A; the second branch duct 51B is provided with a second electromagnetic valve 52B. Further, a pressure reducing valve 54 is provided upstream to the first and second branch ducts 51A and 51B forming the branch-confluent portion.

The first and second electromagnetic valves 52A and 52B are each a valve for changing an amount of supply of the dry gas P while the electromagnetic valve controller 53 controls the opening and closing of the flow paths as described above. The electromagnetic valve controller 53 is connected with the CPU 40. The electromagnetic valve controller opens the flow paths of the first and second electromagnetic valves 52A and 52B in response to control operations of an opening time dry process and a closing time dry process to be described later, and lets the dry gas P flow into the purge box 11.

When the first electromagnetic valve 52A is opened, a predetermined amount of flow (which is of the dryness-maintaining gas P1) flows into the purge box 11. Further, when the second electromagnetic valve 52B is opened, a predetermined amount of flow (which is of the additional dry gas P2) flows into the purge box 11. Specifically, when both the electromagnetic valves 52A and 52B are left open, a large amount of dry gas P as large as e.g. about 1 to 5 L/min can be supplied.

The furnace body portion-drying means of the invention herein refers to a combination of the heater block temperature-controlling means and the dry gas supplying means 50 (gas-inflow means), which have been described above.

Also, in the thermal analysis system 10 is disposed the purge gas duct 60 for supplying a purge gas into the heat sink 12 from the outside through a mass flow 61. As the purge gas, an inert gas such as nitrogen gas, helium gas, or argon gas is used herein. The mass flow 61 is adjusted so that the purge gas flows into the heat sink 12 at an amount of flow of e.g. about 50 mL/min during the time of measurement, under the condition where the control of a mass flow controller 62 controls the amount of flow of the purge gas.

Next, the drying method in the thermal analysis system 10 will be described with reference to the drawings including an operation flow chart and a sequence diagram.

The drying method is a method includes automatically controlling an opening time dry process which is started when a user performs an action to turn on the main power source of the thermal analysis system 10 shown in FIG. 1, and a closing time dry process which is started when a user performs a manipulation for ordering the end-of-work at the end of measurement. Herein, the dry condition corresponding to the connection mode of the cooling device 30 has been set in the CPU 40 in advance.

An operation flow (drying method) of the opening time dry process will be described, first.

As shown in FIGS. 1 and 3, when a user turns on (activates) the power source of the thermal analysis system 10 by hand at Step S1, the first electromagnetic valve 52A for the dryness-maintaining gas P1 is opened (Step S2). In parallel with this, the temperature control module 21 controls the heater 14 so that a standby temperature K1 in the purge box 11 is made e.g. 30° C. (Step S3) (see FIG. 4). As a result, the dryness-maintaining gas P1 is made to go through the first branch duct 51A at an amount of gas flow of e.g. 0.5 l/min and ends up being supplied into the thermal analysis system 10 (purge box 11). Incidentally, it is preferable that the standby temperature K1 is set within a range of 30 to 40° C.

Subsequently, at Step S4, the user selects the cooling method, i.e. the type of the cooling device 30 connected with the thermal analysis system 10 (cooling block 16). Specifically, one of electric cooling (the electric cooling device 30B) and non-electric cooling (i.e. the case of using the liquid nitrogen type cooling device 30A or the case of not using the cooling device 30) will be selected. The action for the selection at Step S4 is herein performed using the PC machine 42.

In the case where the non-electric cooling has been selected at Step S4 (the case where the liquid nitrogen type cooling device 30A has been connected with the cooling block 16 as the cooling device 30 here), the operation flow proceeds to Step S10. Then, the second electromagnetic valve 52B is brought to ON and opened, and the additional dry gas P2 flows through the second branch duct 52B. As a result, the additional dry gas P2 is supplied into the thermal analysis system 10 (purge box 11) in addition to the dryness-maintaining gas P1, and the drying operation is started (see FIG. 4). Subsequently, the first drying time T1 is set to e.g. 60 minutes, as shown in FIG. 4. It is preferable that the drying temperature K2 during this time is 100° C. or higher. Hence, the drying temperature is set to 125° C., for example (Step S11). In addition, the amount of gas flow of the additional dry gas P2 is set to e.g. 1 to 5 L/min.

When it is confirmed that the first drying time T1 has elapsed (Step S12: YES), the drying operation is terminated (Step S13). Then, the second electromagnetic valve 52B is closed, whereby supply of the additional dry gas P2 is stopped. In addition, as shown in FIG. 4, only the dryness-maintaining gas P1 is supplied into the purge box 11, whereby the dry state is kept continuously (Step S14). Further, the standby temperature K3 at that time is controlled so as to be the same as the standby temperature K1 before the drying operation, e.g. 30° C. (Step S15). A series of the steps so far form the operation flow of the opening time dry process, by which measurement preparation is completed (Step S16).

Now, an operation flow in the case where electric cooling is selected at Step S4, which has been described with reference to FIG. 3, will be described with reference to FIGS. 5 and 6, and others.

FIG. 5 shows an operation flow in the case where electric cooling is selected. As Steps S1 to S4 are the same as those in the case where the non-electric cooling is selected as described above with reference to FIG. 3, their descriptions are omitted.

As shown in FIGS. 1 and 5, in the case where electric cooling (the electric cooling device 30B) is selected at Step S4, the operation flow proceeds to Step 20. Then, the second electromagnetic valve 52B is brought to ON and opened, and the additional dry gas P2 flows through the second branch duct 51B. As a result, the additional dry gas P2 is supplied into the thermal analysis system 10 (purge box 11) in addition to the dryness-maintaining gas P1, and the drying operation is started (see FIG. 6). The dry process on this occasion is referred to as the primary dry process.

As shown in FIG. 6, the second drying time T2 is set to e.g. 60 minutes, and the heat sink control temperature K4 (which corresponds to the first temperature of the invention) is set to e.g. 125° C. (Step S21). Incidentally, the amount of gas flow of the additional dry gas P2 in this case is set to e.g. 1 to 5 L/min. In addition, the power source of the electric cooling device 30B at this time is in OFF (a down state), and the dryness-maintaining gas P1 and the additional dry gas P2 are continuously supplied. It is preferable that during the time of the primary dry process, the control temperature K4 is set to a heat sink control temperature (which is set to 125° C. as described above in this embodiment) such that the leading end (a portion inserted in the cooling block 16) of the electric cooling device 30B which is not working is never damaged owing to a high temperature.

When it is confirmed that the second drying time T2 (60 minutes) has elapsed (Step S22: YES), the ON/OFF control panel 31 turns ON the power source of the electric cooling device 30B, and the cooling block 16 is cooled. Then, at the time when a predetermined time (which is defined as a first fixed time T3, and set to e.g. 10 minutes) has elapsed since the electric cooling device 30B is turned ON, confirmation of connection of the electric cooling device 30B is executed at Step S23. Specifically, at Step S23, the control temperature of the heat sink 12 in the thermal analysis system 10 (which is defined as a checking temperature K5) is set to e.g. 5° C. and controlled to the checking temperature K5 for e.g. 5 minutes (which is defined as a second fixed time T4).

Then, when the temperature of heat sink 12 reaches the checking temperature K5 (5° C.) with the electric cooling device 30B working (Step S23: YES), the operation flow proceeds to Step S25. In contrast, when the temperature of the dry gas P in the thermal analysis system 10 does not reach the set checking temperature K5 (5° C.) (Step S23: NO), it is judged that the cooling device 30 is not working normally, and e.g. an error notice is presented at Step S24.

As the case of NO at Step S23 are presumed the case where the electric cooling device 30B (cooling rod) is not mounted (the case where the liquid nitrogen type cooling device 30A or the like is connected) and a failure of the electric cooling device 30B, etc. In other words, in the case of a cooling device other than the electric cooling device 30B and the case where no cooling device is connected, the temperature does not lower to 5° C., and therefore it is required to e.g. properly set the connection mode of the cooling device 30 again thereby to reconfirm the connection mode. When the electric cooling device 30B is connected properly, the temperature lowers to the control temperature of 5° C.

Next, when it is judged at Step S23 that the electric cooling device 30B is connected and actuated properly, the temperature control is performed under the condition where the electric cooling device 30B is left to work so that the heat sink control temperature K6 (which corresponds to the second temperature of the invention) is made e.g. 450° C., and the secondary dry process is started (Step S25). The third drying time T5 during this time is set to e.g. 45 minutes. In other words, the time between the start of the primary dry process and the termination of the secondary dry process is two hours.

Then, when it is confirmed that the third drying time T5 (45 minutes) has elapsed (Step S26: YES), and the drying operations of the two stages (the primary dry process and the secondary dry process) are terminated (Step S27), the second electromagnetic valve 52B is closed, whereby supply of the additional dry gas P2 is stopped. Thus, as shown in FIG. 6, only the dryness-maintaining gas P1 is supplied into the purge box 11, whereby the dry state is maintained (Step S28). Then, the standby temperature K7 during the time is set so as to be a temperature which is the same as the standby temperature K1 before the drying operation, e.g. 30° C. (Step S29). The flow described so far is the operation flow of the opening time dry process in the case where the electric cooling device 30B is connected, and then the measurement preparation is completed (Step S201).

In the case of cooling by liquid nitrogen as described above, the cooling can be stopped by stopping supply of the gas. However, in the case of electric cooling, the opening time dry process is performed by primarily drying the inside of the system at the drying temperature K4 (125° C.) so high as not to damage the cooling module (cooling rod) of the electric cooling device 30B, thereafter actuating the electric cooling device 30B to cool a surrounding portion of the cooling block 16, and then raising the control temperature into the higher drying temperature K6 (450° C.) to secondarily dry the inside of the system. By drying the inside of the system in the two stages of the primary dry process and the secondary dry process in this manner elaborately, the moisture including condensation and frost, which has adhered to the inside of the system before actuation of the cooling device 30, can be removed without fail. In other words, part of the moisture which cannot be removed through the primary dry process perfectly can be removed through the secondary dry process thereby to finish the opening time dry process.

Incidentally, the operation of selecting whether or not to execute a drying task may be interposed between Step S4 and Step S10 (Step S20), which is not shown in the drawing particularly. Control may be performed so that when the task is to be executed, the operation flow proceeds to Step S10 (Step S20), while when the task is not to be executed, the drying task after that is not performed, and the operation flow goes into the stage of measurement preparation.

Now, the operation flow (drying method) in the closing time dry process will be described with reference to FIGS. 7 and 8. Here, in the closing time dry process, the operation flow is common to the electric cooling device 30B and the liquid nitrogen type cooling device 30A regardless of their cooling method.

As shown in FIG. 7, when the power source of the thermal analysis system 10 is cut off after the completion of measurement of the sample M (Step S30), the user performs a manipulation for ordering the end-of-work through the PC machine 42 at Step S31. The dry gas P supplied into the purge box 11 in this stage is only the dryness-maintaining gas P1, whose standby temperature K1 is temperature-controlled so as to be 30° C. as described above (see FIG. 8). Further, the cooling device 30 is in its working state.

Subsequently, at Step S32, the cooling device 30 is turned OFF. At Step S33, the second electromagnetic valve 52B is turned ON and opened. Then, the additional dry gas P2 begins to flow through the second branch duct 51B. Thus, the additional dry gas P2 in addition to the dryness-maintaining gas P1 are supplied into the thermal analysis system 10 (purge box 11), and the drying operation is started. As shown in FIG. 8, the fourth drying time T6 is set to e.g. 120 minutes. It is preferable that the heat sink control temperature K8 on this occasion is set to a temperature a bit higher than a room temperature for example, and it is set to e.g. 40° C. (Step S34). In addition, the amount of gas flow of the additional dry gas P2 is made 1 to 5 L/min, for example.

Then, it is confirmed that the fourth drying time T6 has elapsed (Step S35: YES), and the drying operation is terminated (Step S36). The second electromagnetic valve 52B is closed thereby stop supply of the additional dry gas P2. Only the dryness-maintaining gas P1 is supplied into the purge box 11 as shown in FIG. 8. Thereafter, the first electromagnetic valve 52A is closed to stop the supply of the dryness-maintaining gas P1 in a predetermined time. That is, the amount of flow of the dry gas is made zero (Step S37). The standby temperature K9 on that occasion is set so as to be e.g. 30° C. (Step S38).

Subsequently, at Step S39 the main power cutoff device 41 is actuated, whereby the power source of the thermal analysis system 10 is turned OFF. The flow described so far is the operation flow of the closing time dry process.

As described above, the closing time dry process can prevent condensation from occurring inside the purge box 11 when the thermal analysis system 10 is used the next time. Particularly in the case of using the electric cooling device 30B, the cooling block 16 remains cooled for a while even after the power source of the thermal analysis system 10 has been cut, and condensation sometimes occurs around the cooling block. However, such cooled state in the purge box 11 can be prevented by performing the closing time dry process, whereby the occurrence of condensation like this can be suppressed.

Further, in the closing time dry process, the inside of the system is dried at a lower temperature for a longer time in comparison to the opening time dry process. Therefore, even when the user forgets to unload the sample M after measurement, and thus the sample is left in the thermal analysis system 10, the trouble that the sample M melts to damage the sensor module can be avoided because the drying temperature is not so high but the same as that of a surrounding portion of the thermal analysis system 10.

As described above, in the thermal analysis system in accordance with the embodiment and its drying method, the inside of the purge box 11 begins to be dried upon activation of the thermal analysis system 10, and therefore the moisture including condensation and frost, which has adhered to the inside of the system before actuation of the cooling device 30, can be removed at the time before measurement without fail. Hence, the noise generation in measured data owing to such moisture is avoided and a precise measurement can be performed.

In addition, the furnace body portion-drying means which performs dry control of the dry conditions depending on the connection mode of the cooling device 30, such as an amount of supply of the dry gas P, a time for the supply, and a drying temperature, can eliminate the labor to manage the dry conditions through a manual manipulation as in a conventional case, and thus the inside of the system can be dried efficiently and without fail.

Further, in the case where the system 10 is not used for a long time, the system can be dried appropriately in using the system even if the dry gas is not kept flowing.

The thermal analysis system in accordance with the embodiment can be made to control an operation of drying the inside of the purge box 11 by performing a manipulation for ordering the end-of-work at the closing time. Therefore, it is possible to avoid the occurrence of condensation inside the purge box 11 when the thermal analysis system 10 is used next time.

While the embodiments of the thermal analysis system in accordance with the invention and its drying method have been described, the invention is not limited to the above-described embodiments. Changes and modifications may be made appropriately without departing from the subject matter thereof.

For instance, the dry conditions for the opening time dry process and the closing time dry process, i.e. specific conditions including amounts of supply of the dryness-maintaining gas and the additional dry gas, drying temperatures, drying times, and the timing of ON/OFF of the cooling device, and others may be set by a user arbitrarily depending on the installation condition of the thermal analysis system and a sample used. While in the embodiment, the cooling methods corresponding to the dry conditions to be selected are electric cooling and non-electric cooling, the methods are not limited to the two types.

Further, while in the embodiment, in the opening time dry process by the electric cooling device, drying is performed at the drying temperatures in association with two stages of the primary dry process and the secondary dry process, such drying may be performed through three or more stages of dry processes.

What is claimed is:

1. A thermal analysis system having a furnace body portion including a heater block into which a specimen is loaded, a cooling block connected with the heater block, and a purge box making an outside housing of the heater block and cooling block, the thermal analysis system comprising:
a furnace body portion-drying means for drying the furnace body portion for a predetermined time in response to activation of the thermal analysis system, the furnace body portion-drying means comprising:
a gas-inflow means for letting a drying gas flow into the furnace body portion: and
a heater block temperature-controlling means for controlling a temperature of the heater block,
wherein the furnace body portion-drying means changes a gas-inflow condition and a control temperature condition depending on a type of a cooling device connected with the cooling block
wherein when the cooling device is an electric cooling device, the heater block temperature-controlling means makes the temperature of the heater block a first temperature with the cooling device kept off, and makes the temperature a second temperature higher than the first temperature after confirmation of activation of the electric cooling device.

2. A thermal analysis system having a furnace body portion including a heater block into which a specimen is loaded, a cooling block connected with the heater block, and a purge box making an outside housing of the heater block and cooling block, the thermal analysis system comprising:
furnace body portion-drying means for drying the furnace body portion for a predetermined time before a power source is shut off in response to a manipulation for ordering end-of-work of the thermal analysis system, the furnace body portion-drying means comprising:
a gas-inflow means for letting a drying gas flow into the furnace body portion; and
a heater block temperature-controlling means for controlling a temperature of the heater block,
wherein the furnace body portion-drying means changes a gas-inflow condition and a control temperature condition depending on a type of a cooling device connected with the cooling block
wherein when the cooling device is an electric cooling device, the heater block temperature-controlling means makes the temperature of the heater block a first temperature with the cooling device kept off, and makes the temperature a second temperature higher than the first temperature after confirmation of activation of the electric cooling device.

3. A method of drying a thermal analysis system having a heater block for heating a specimen, a cooling block connected with the heater block, and a purge box making an outside housing of the heater block and cooling block, the method comprising:

setting a dry condition depending on a connection mode of the cooling device;

starting control of an opening time dry process simultaneously with activation of the thermal analysis system;

selecting the connection mode of the cooling device; and drying the furnace body portion before thermal analysis measurement of the specimen; and drying the furnace body portion before thermal analysis measurement of the specimen upon activation of the thermal analysis system and in accordance with the dry condition corresponding to the selected cooling device connection mode;

wherein when the cooling device is an electric cooling device, the temperature of the heater block is controlled to primarily dry the system at a first temperature with the electric cooling device kept off, and then the cooling device is actuated to secondarily dry the system at a second temperature higher than the first temperature.

4. The method of drying a thermal analysis system in accordance with claim 3, further comprising:

supplying a dry gas into the purge box, and managing a temperature of the heater block with a temperature control module thereby to control a drying operation.

5. The method of drying a thermal analysis system in accordance with claim 3, wherein when the cooling device is an electric cooling device, a connection mode of the thermal analysis system and the electric cooling device is confirmed before the secondary drying is performed.

6. The method of drying a thermal analysis system in accordance with claim 3, wherein when a manipulation for ordering end-of-work of the measurement is performed, control of a closing time dry process is started, and a drying operation is performed by supplying a predetermined amount of the dry gas into the purge box.

7. The method of drying a thermal analysis system in accordance with claim 6, wherein after the drying operation in the closing time dry process has been terminated, performing control so that a power source of the thermal analysis system is cut off automatically.

8. The method of drying a thermal analysis system in accordance with claim 6, wherein drying is performed at a temperature the same as that of a surrounding portion of the thermal analysis system in the closing time dry process.

* * * * *